United States Patent [19]

Mitchell et al.

[11] Patent Number: 5,452,084
[45] Date of Patent: Sep. 19, 1995

[54] METHOD AND APPARATUS FOR ZERO-CALIBRATION OF A RAMAN SPECTROSCOPY SYSTEM

[75] Inventors: John Mitchell, Salt Lake City; Scott D. Miles, Sandy; Donald E. Gregonis, Salt Lake City; Kent F. Beck, West Valley City, all of Utah

[73] Assignee: Albion Instruments, Inc., Liberty Corner, N.J.

[21] Appl. No.: 38,177

[22] Filed: Mar. 29, 1993

[51] Int. Cl.⁶ .......................... G01J 3/44; G01N 21/65
[52] U.S. Cl. ................................. 356/301; 356/307; 250/282; 250/286
[58] Field of Search .............. 356/301, 307, 338, 246; 250/286, 282, 287, 576

[56] References Cited

U.S. PATENT DOCUMENTS

| | | | |
|---|---|---|---|
| 3,911,276 | 10/1975 | Bell | 250/343 |
| 4,630,923 | 12/1986 | Tans et al. | 356/301 |
| 4,648,714 | 3/1987 | Benner et al. | 356/301 |
| 4,676,639 | 6/1987 | Van Wagenen | 356/301 |
| 4,720,160 | 1/1988 | Hicks, Jr. | 350/96.15 |
| 4,784,486 | 11/1988 | Van Wagenen et al. | 356/301 |
| 4,889,987 | 12/1989 | Gruen et al. | 250/282 |
| 5,135,304 | 8/1992 | Miles et al. | 356/301 |
| 5,153,671 | 10/1992 | Miles | 356/301 |
| 5,245,405 | 9/1993 | Mitchell et al. | 356/301 |

FOREIGN PATENT DOCUMENTS 0058444 7/1983 Japan .

OTHER PUBLICATIONS

Brumbach, Stephen B., et al., "In–Cavity Laser Raman Spectroscopy of Vapors at Elevated Temperatures. As₄ and As₄O₆", *The Journal of Chemical Physics*, vol. 56, No. 6, Mar. 1972, pp. 3110–3117.

Smith, J. E. Jr., "Laser System for Measurements of Gas Concentrations in Mixtures of Gases", *IBM Technical Disclosure Bulletin*, vol. 16, No. 6, Nov. 1973, pp. 1804–1805.

Weber, Alfons, et al., "High–Resolution Raman Spectroscopy of Gases With Laser Sources, V. Use of the Single–Mode Argon Laser", *Journal of the Optical Society of America*, vol. 62, No. 3, Mar. 1972, pp. 428–432.

Smith, Lee M., et al., "Raman Spectroscopy for On–Line Multiple Component Gas Analysis", *Advances in Instrumentation and Control* Part 2–Research Triangle Park, N.C., vol. 45, 1990, pp. 711–720.

*Primary Examiner*—Robert P. Limanek
*Assistant Examiner*—Alexander Oscar Williams
*Attorney, Agent, or Firm*—Roger M. Rathbun; Larry R. Cassett; Dennis H. Epperson

[57] ABSTRACT

A Raman spectroscopy system and method for determining a zero-calibration level. A gas sample chamber is located within a resonant cavity. A light source is located to cause light to be incident on the gas sample, the light resonates in the resonant cavity. Typically, the light source and resonator cavity in conjunction form a laser source which propagates coherent, monochromatic laser light energy through the gas sample. This causes Raman scattering from the gases constituent in the gas sample. The amount of Raman scattered light is measured at detectors along with light due to dark noise inherent in the detectors and glow from the laser source, i.e., light at wavelengths other than the laser light wavelength produced by the laser source. The resonator cavity is obstructed, via a ball inserted into the path of the laser beam for example, to prevent resonance. If the light source and resonant cavity in conjunction form a laser, prevention of resonance causes cessation of lasing. Thus, substantially no Raman scattering occurs and detectors measure light due primarily to background noise. The origin of the measurement scale for the detectors may then be set at the measured intensity, i.e., a zero-calibration level for the detectors may be determined.

19 Claims, 11 Drawing Sheets

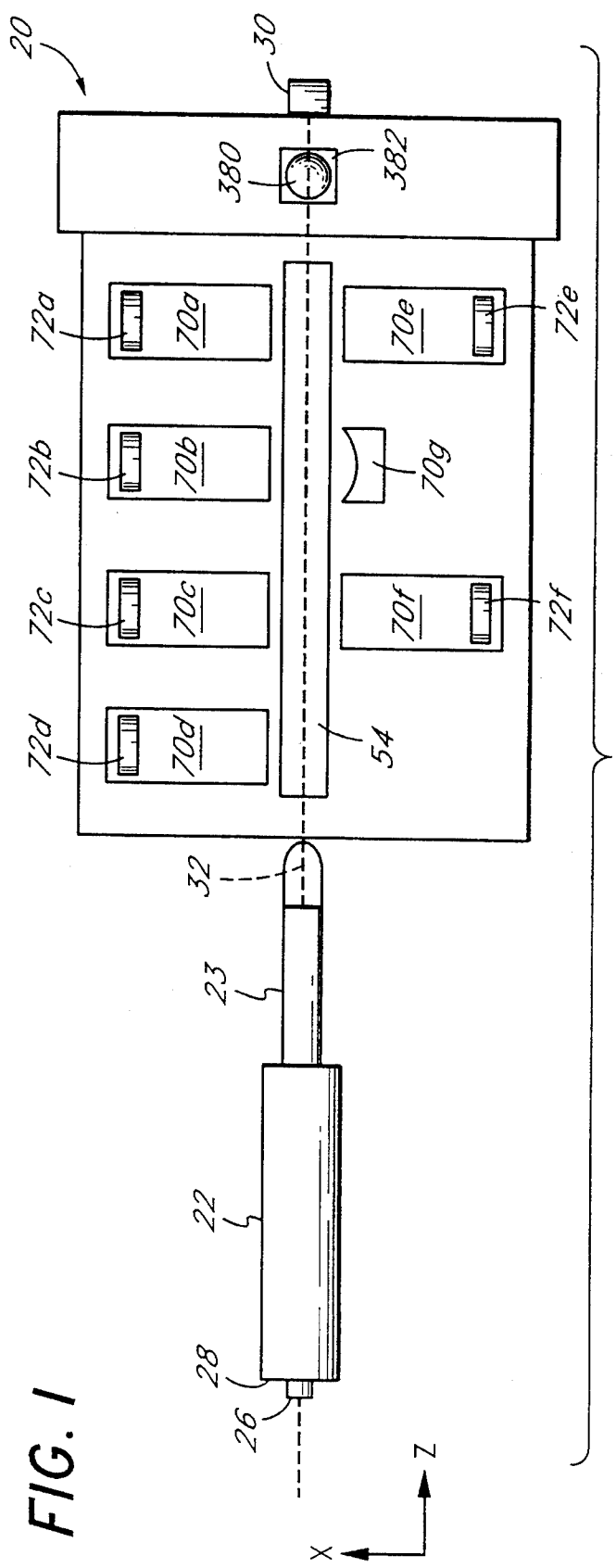
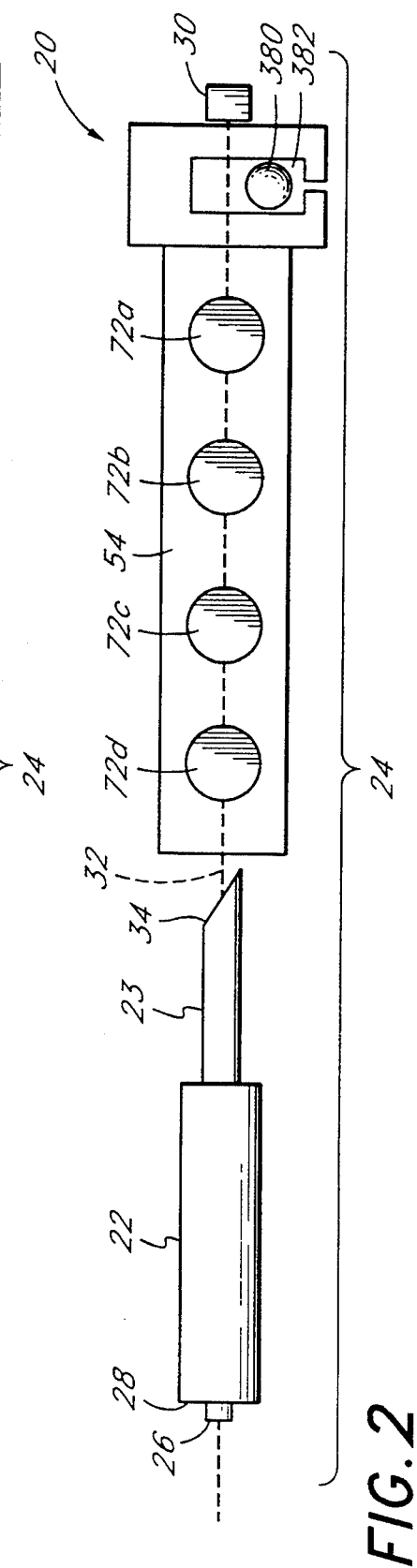
FIG. 1
FIG. 2

METHOD AND APPARATUS FOR ZERO-CALIBRATION OF A RAMAN SPECTROSCOPY SYSTEM

FIELD OF THE INVENTION

The present invention relates to an improved Raman spectroscopy system. More specifically, the present invention relates to apparatuses and methods for zero-calibration in gas analysis systems. The invention is disclosed in the context of a Raman spectroscopy gas analysis system.

BACKGROUND OF THE INVENTION

When an incident photon collides with a polyatomic gas molecule, it may either be scattered elastically, i.e., without energy exchange, or inelastically, i.e., with energy exchange that excites or de-excites a rotational/vibrational mode of the molecule. If the incident photon collides with a gas molecule and excites the gas molecule to a higher vibrational/rotational energy mode, the photon is re-emitted at a lower energy and consequently lower frequency than the incident photon. This inelastic scattering is termed Stokes Raman scattering. Similarly, if the incident photon collides with a gas molecule and de-excites the gas molecule to a lower vibrational/rotational energy mode, the photon is re-emitted at a greater energy and consequently higher frequency than the incident photon. This type of inelastic scattering is termed anti-Stokes Raman scattering. Although both effects may be observed, at room temperatures the Stokes Raman effect is generally more intense and thus, easier to measure. Therefore, the light resulting from collisions according to the Stokes Raman effect is typically analyzed and will be discussed herein.

Rotational/vibrational energy modes of molecules are quantized, forcing photons to exchange energy with molecules in discrete amounts. Different gas molecules require different amounts of energy from a photon to excite molecules to a higher rotational/vibrational mode. Thus, the amount of energy necessary to excite a gas molecule to a higher mode is characteristic of the type of molecule. The change in the photon's frequency caused by inelastic scattering corresponds to the amount of energy lost by the photon and can be used to identify the type of molecule which caused the scattering. Such analysis is called Raman spectroscopy.

Raman spectroscopy systems typically comprise a laser which directs intense, monochromatic light energy toward a gas sample to be analyzed. Detectors, such as photo multiplier tubes or avalanche photodiodes, are arranged about the gas sample to receive Raman scattered energy. Filters remove elastically scattered energy at the wavelength of the laser source. Additional filters, each filter being designed to pass a different wavelength of expected Raman scattered energy, or a different Raman line, are placed in front of different detectors. As many detectors may be utilized as there are expected Raman lines. U.S. Pat. No. 4,784,486 to Van Wagenen et al., describes one type of multi-channel system. Alternatively, a rotating filter which passes different Raman lines as it rotates may be employed with a single detector. U.S. Pat. No. Re. 34,153 to Benner et al., describes one type of single channel system. The amount of energy collected on each detector corresponds to the concentration of the gas which created the particular Raman line.

Although there are filters between the gas sample and the detectors in the Raman spectroscopy system, light at wavelengths other than the lasing wavelength produced by the laser source, e.g., laser glow, is often collected by the detector, causing background noise in the measured signal. Additionally, photodetectors often have inherent dark noise which adds to the background noise. For accurate measurements of light due to Raman scattering, the system should be calibrated such that the signal from such background noise at the photodetectors is determined, i.e., a zero-calibration level of the system is set equal to the background noise level. Thus, there exists a need for apparatuses and methods for zero-calibration of Raman spectroscopy gas analysis systems.

SUMMARY OF THE INVENTION

The present invention is for Raman spectroscopy systems and methods for performing zero-calibration. A laser having a light source and a laser resonator cavity causes laser light to be incident on a gas sample which is contained within a resonant cavity, for example, the laser resonator cavity. Detectors are advantageously placed around the gas sample to receive scattered energy.

In one embodiment, an obstruction is placed in the laser resonator cavity which prevents the laser from lasing but which does not obstruct the plasma glow emitted from the laser tube. Without the intense laser light there is only negligible Raman scattering. Thus, the remaining signal measured at the detectors is predominantly due to plasma glow from the light source and dark noise inherent in the detectors. Thus, a zero-calibration level may be determined quickly with the gas sample in the resonant cavity by blocking the lasing light. Elastic scattering from the laser light is rejected by the filters, and therefore does not contribute to the background.

Alternatively, the zero-calibration level may be determined by filling the gas sample chamber with a gas that does not cause Raman scattering. For example, a monatomic gas, such as argon, can be used for this purpose. The laser source is energized and the signal at the detectors is measured. As discussed previously, filters remove light at the laser wavelength and argon gas does not cause Raman scattering. Thus, the intensity measured at the photodetectors is primarily due to plasma glow from the laser source and photodetector dark noise. The zero-calibration level is set at the value of the background thus measured.

In one embodiment, the present invention is a Raman spectrometer comprising: a light source for producing light; a resonant cavity for receiving the light from the light source such that the light resonates within the resonant cavity; a detector in optical communication with the resonant cavity for receiving Raman scattered light from an analysis sample located within the resonant cavity; and a means for altering the optical characteristics of the resonant cavity such that the light from the light source no longer resonates within the resonant cavity, thus reducing the Raman scattered light from the analysis sample detected by the detector to substantially zero. Additionally, the means for altering the optical characteristics may further comprise a blocking device which intercepts the light resonating in the cavity and prevents the light from circulating within the cavity. In some embodiments, the resonant cavity further comprises first and second end reflectors. In this embodiment, the means for altering the optical characteristics further comprises a blocking device which intercepts the light prior to reaching one of the first and second end reflectors. The light source may further comprise a plasma tube. Additionally, the resonant cavity may further comprise a gas sample region for containing a gas sample within the resonant cavity.

In another embodiment, the invention is a spectrometer comprising: a light source for producing light; a resonant cavity for receiving the light from the light source such that the light resonates within the resonant cavity; a detector in optical communication with the resonant cavity for receiving scattered light from an analysis sample located within the resonant cavity; and a means for altering the optical characteristics of the resonant cavity such that the light from the light source no longer resonates within the resonant cavity thus reducing the Raman scattered light from the analysis sample detected by the detector to substantially zero. Additionally, the means for altering the optical characteristics may further comprise a blocking device which intercepts the light resonating in the cavity and prevents the light from circulating within the cavity. In some embodiments, the resonant cavity further comprises first and second end reflectors. In this embodiment, the means for altering the optical characteristics further comprises a blocking device which intercepts the light prior to reaching one of the first and second end reflectors. The light source may further comprise a plasma tube. Additionally, the resonant cavity may further comprise a gas sample region for containing a gas sample within the resonant cavity.

The present invention further includes a method for calibrating an electromagnetic spectrometer having an electromagnetic resonant cavity comprising the steps of: altering the electromagnetic characteristics of the resonant cavity so that it is substantially nonresonant; and deriving a background signal level from the substantially nonresonant cavity. Additionally, the step of altering the electromagnetic characteristics of the resonant cavity may further comprise the step of substantially eliminating the production of predetermined spectroscopy signals, leaving only background and/or noise signals. In many embodiments, the electromagnetic spectrometer further comprises a Raman spectrometer. In this method, the step of altering the electromagnetic characteristics of the resonant cavity may further include the step of reflecting electromagnetic signals. Alternatively, the step of altering the electromagnetic characteristics of the resonant cavity may further comprise the step of absorbing electromagnetic signals, or diffracting electromagnetic signals or refracting electromagnetic signals.

These and other characteristics of the present invention will become apparent through reference to the following detailed description of the preferred embodiments and accompanying drawings.

BRIEF DESCRIPTION OF THE DRAWINGS

FIG. 1 shows a plan view of a schematic representation of a Raman spectroscopy system of the present invention.

FIG. 2 shows a side view of the schematic representation of a Raman Spectroscopy system shown in FIG. 1.

FIG. 4b shows a cross sectional view through the gas sample cell shown in FIG. 4a.

DETAILED DESCRIPTION OF THE INVENTION

Figure 3:
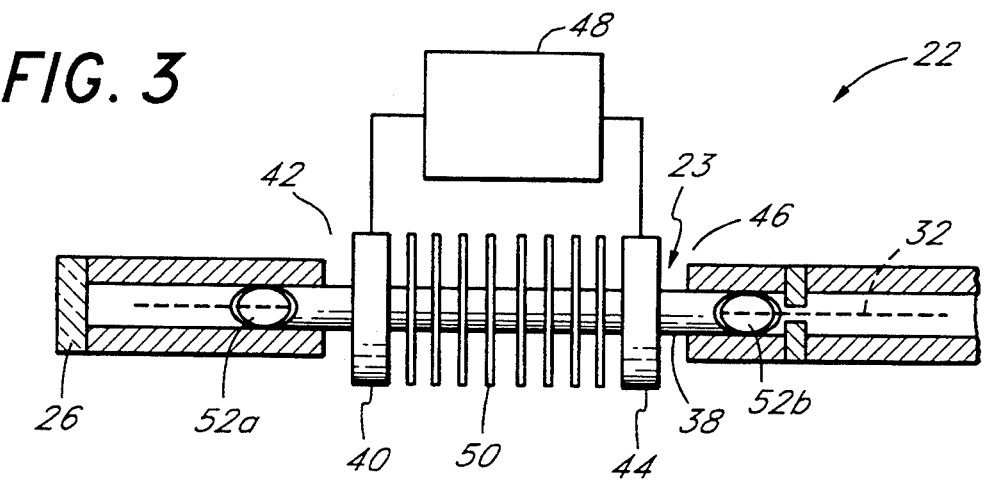
FIG. 3 shows a plan view of one type of Raman spectroscopy system of the present invention wherein a gas sample is located within a laser resonator cavity.

Raman spectroscopy relies on the inelastic scattering of light from polyatomic gas molecules via energy exchange between photons and vibrational/rotational modes of the molecules. When light is made incident on a sample of gas, photons are caused to collide with at least some of the gas molecules in the sample. The photon may gain or lose energy in the amount of a quantized rotational/vibrational mode of a molecule. Such a gain or loss results in a shift in the frequency of the scattered photon from the frequency of the incident photon. Correspondingly, the wavelength of the scattered photon also shifts. Statistically, at low temperatures, more photons lose energy to the gas molecules, causing a more intense Raman scattered signal at longer light wavelengths than the incident light. By comparing frequency shifts caused in a sample of gas to known frequency shifts from a particular wavelength of incidence, the type, or types, of gas present in the sample may be ascertained. By filtering out all but expected wavelengths of Raman scattered light, or Raman lines, and determining the amount of energy collected at each detector versus the total energy collected, the percentage constituency of a gas sample may also be determined. Monochromatic light facilitates the analysis of a plurality of gases simultaneously by providing a known wavelength of incidence.

Raman scattering systems may be arranged having a sample of gas to be analyzed located within a resonant cavity which contains a light source to supply light for Raman scattering. One such Raman spectroscopy system is described in U.S. Pat. No. 4,784,486 to Van Wagenen, et al., hereby incorporated herein by reference, wherein the gas sample is located within a resonator cavity which also provides resonance for laser gain. This configuration, where the gas sample is located within the resonant cavity of the laser, is often referred to as intracavity gas sample placement.

FIGS. 1 and 2 schematically show an intracavity collimated beam Raman spectroscopy system 20 comprising a gain mechanism 22 arranged within a laser resonator cavity 24 defined by a first mirror 26 adjacent a first end 28 of the gain mechanism 22 and a second mirror 30 opposite the first mirror 26 and the gain mechanism 22.

The gain mechanism 22 emits a beam 32 which is reflected back and forth within the resonant cavity 24 by the mirrors 26 and 30. Collimators (not shown) may be located adjacent a second end 34 of the gain mechanism 22, positioned to cause the light beam 32 to become substantially collimated as the beam 32 travels back and forth in the resonant cavity 24. If the gain mechanism 22 produces a low divergence beam 32, the collimators may not be necessary. This is often the case when the gain mechanism 22 and mirrors 26 and 30 form a laser. Laser light is generally preferable in Raman scattering applications and will be discussed herein. More particularly, gas lasers utilizing a plasma tube as the gain mechanism 22 are employed in many Raman spectroscopy systems. However, it will be understood that other types of gain mechanisms 22 may be utilized.

The laser in one embodiment of the present invention is a gas laser, such as a continuous wave argon ion laser capable of producing a polarized beam 32 of light having a wavelength of approximately 488 nanometers. Alternatively, the laser could be a helium neon laser producing a beam of light having a wavelength of approximately 632.8 nanometers. Other types of lasers, including carbon dioxide lasers, solid state lasers and semiconductor diode lasers, for example, may also be employed.

The laser is made up of a gain mechanism, herein called a laser plasma tube, 22 and the first and second mirrors 26 and 30 which form the resonant cavity 24 for creating laser gain. The laser plasma tube 22 of an argon laser as shown in FIG. 3, comprises a plasma discharge tube 38, a cathode 40 located near one end 42 of the discharge tube 38 and an anode 44 located near the opposite end 46 of the discharge tube 38. A power supply 48 is connected to the cathode 40 and anode 44. A heat exchanger 50 thermally contacts and surrounds a portion of the discharge tube 38 located between the cathode 40 and anode 44. A lasing gas mixture containing argon gas is confined within the plasma discharge tube 38 having Brewster windows 52a and 52b at both ends 42 and 46 to allow light of a preferred polarization state to pass without substantial loss. The laser plasma tube 22 of a helium neon laser is similar to that shown in FIG. 3, except that the plasma discharge tube 38 contains a mixture including helium and neon gases, and the Brewster window 52a at the first end 42 of the plasma tube 22 is removed. In either case, the Brewster window 52b and a nearby portion of the discharge tube 38 at the second end 46 of the plasma tube 22 are often referred to as a Brewster stub 23.

The power supply 48 provides a high voltage between the cathode 40 and anode 44, thus creating a plasma discharge through the lasing gas mixture within the plasma discharge tube 38. Argon atoms contained in the gas mixture are excited to higher energy levels. As these atoms de-excite, photons at many different wavelengths are emitted, many of which are at the wavelength which the laser resonator cavity 24 is built to amplify. These resonate within the cavity 24 until enough gain has occurred to cause population inversion and lasing begins.

Referring back to FIGS. 1 and 2, a sample of one or a plurality of gases to be analyzed is placed in a gas sample chamber 54 located in the path of the laser beam 32 between the gain mechanism 22 and the second mirror 30. Two alternative structures may be employed to contain the sample of gas to be analyzed. The first is a closed chamber having Brewster windows at each end. The second is an artificial chamber created by flowing fluid, such as an inert gas, across each end of the artificial chamber to isolate the sample gas as described in U.S. patent application Ser. Nos. 522,533 and 771,625, now issued as U.S. Pat. Nos. 5,153,671 and 5,135,304, respectively.

Figure 4A:
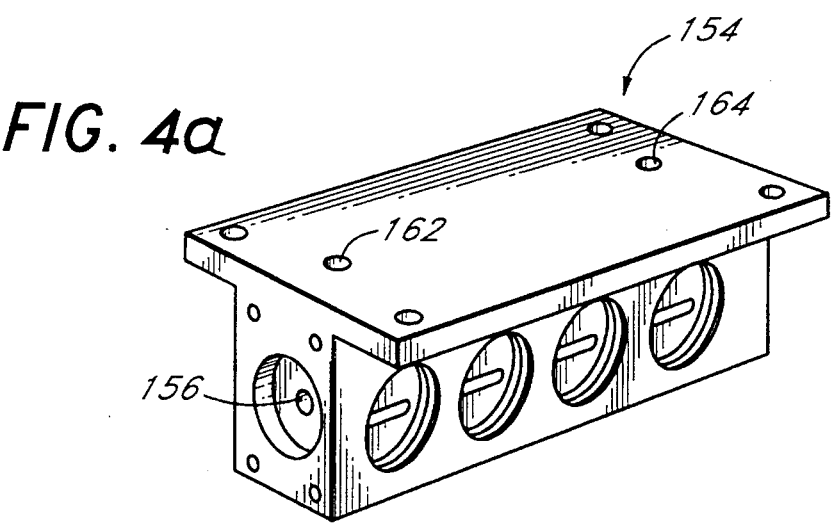
FIG. 4a shows a perspective view of a gas sample cell used in a Raman spectroscopy system.
Figure 4B:
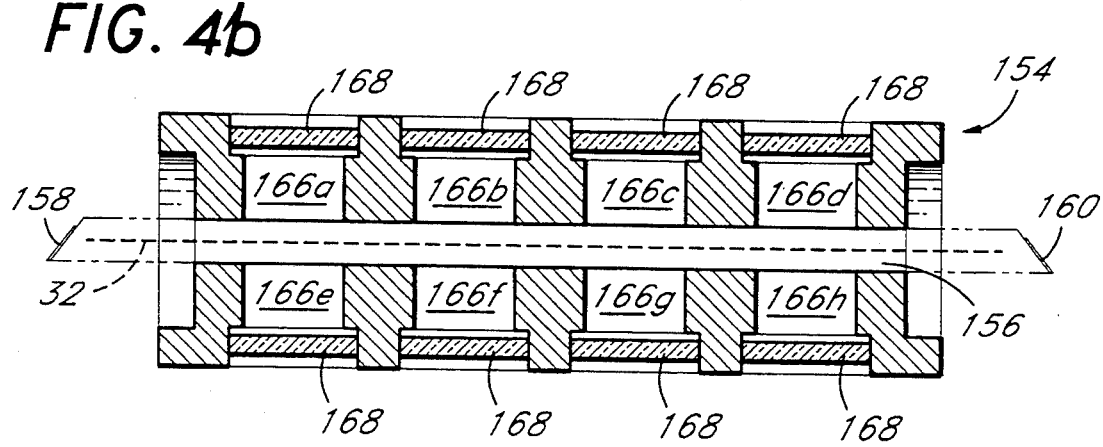

FIGS. 4a and 4b show an embodiment of the enclosed gas sample chamber, labelled herein 154, comprising a hollow central chamber 156 configured to contain a sample of gas. The central chamber 156 is advantageously formed in a generally cylindrical shape so that gas does not collect in any localized region. The volume of the central chamber 156 is made as small as possible so that response time is fast, yet great enough to provide an adequate volume of gas to be analyzed and to provide an unobstructed path for the laser beam as it travels through the central chamber 156. The central chamber 156 is typically aligned having its longitudinal axis generally parallel to the laser beam 32. Both ends of the sample chamber 156 are formed having Brewster windows 158 and 160, aligned so as to cause a predetermined polarization of laser light to pass. It will be understood that other shapes and sizes for the central chamber 156 may be advantageously utilized in the present invention.

Sample gas is drawn into and out of the central chamber 156 via an inlet tube 162 and an outlet tube 164, respectively. A flowmeter (not shown) is connected to the outlet 164 from the central chamber 156. If, for example, the inlet 162 or outlet 164 becomes clogged, the flow through the central chamber 156 will drop. The flowmeter monitors the flow of the sample gas and alerts a user if the flow of the sample gas has dropped below a predetermined level.

Raman scattered light passes through apertures or windows in the walls of the central chamber 156 into channels 166a through 166h, referred to herein collectively as channels 166. Side windows 168a through 168h, referred to herein collectively as windows 168, are mounted along the sides of the gas sample chamber 154. These side windows 168 may either be continuous along the length of the sample chamber 154 or they may be discrete windows mounted at the ends of the channels 166. The side windows 168 transmit Raman scattered light. Thus, the windows 168 may advantageously have a high efficiency broadband anti-reflection coating which passes a large percentage of the light having wavelengths in the range of expected Raman scattering without substantial reflection of energy back into the central chamber 156. The side windows 168 may be coated with a V-band dielectric coating to reject elastically scattered laser wavelength light.

Figure 5:
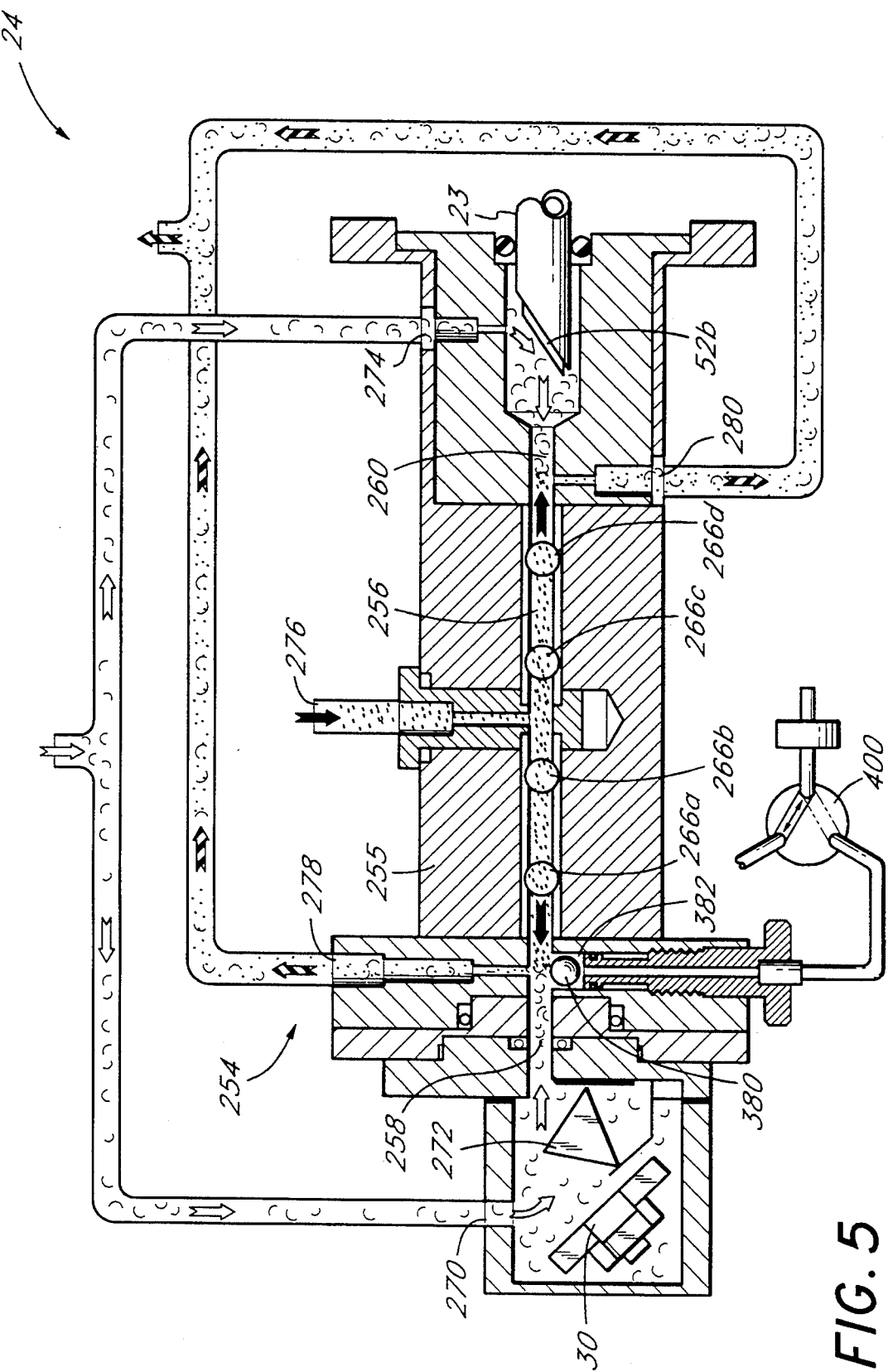
FIG. 5 shows a sectional view of a second type of Raman spectroscopy system of the present invention wherein a gas sample is located within a laser resonator cavity.

FIG. 5 shows a side view of an embodiment of a Raman spectroscopy system having a sample chamber, labelled 254 herein, created by flow of a fluid at the ends of the chamber. Typically, the fluid is air which does not interfere with measurement of Raman scattered light from the gas sample since it does not enter the analysis chamber. Systems of this type are described in application Ser. No. 07/522,533 filed May 11, 1990, by Scott D. Miles, issued as U.S. Pat. No. 5,153,671 and application Ser. No. 07/771,625 filed Oct. 4, 1991, by S.D. Miles, et al., issued as U.S. Pat. No. 5,135,304, both patents hereby incorporated herein by reference. The chamber 254 comprises a housing 255 enclosing a central chamber 256 having buffer regions 258 and 260 at each end formed of the inert gas. Channels 266a through 266h (only four are shown), referred to herein as 266, for catching Raman scattered light are formed adjacent the central chamber 256, similar to the channels 166 in the above described enclosed sample chamber 154.

A first buffer gas inlet port 270 is located adjacent the second mirror 30, within the laser resonator cavity 24. It will be noted that, in this embodiment of an air dam-type sample chamber 254, the second mirror 30 is mounted off the axis of the laser beam 32 and a Brewster prism 272 is used to direct the laser light towards the second mirror 30. The Brewster prism 272 is aligned such that its angular orientation with respect to the laser beam 32 advantageously selects the wavelength of light for which the resonant cavity 24 provides optimum laser gain at a predetermined wavelength. It will additionally be noted that only the Brewster stub 23 of the laser plasma tube 22 is shown in FIG. 5 and the remainder of the Raman spectroscopy system, including the first mirror 26 of the laser resonator cavity, is not shown. A second buffer gas inlet port 274 is connected to the first buffer gas inlet port and is located adjacent the Brewster window 52b of the laser plasma tube 22. A sample gas inlet port 276 is located at approximately the center of the central chamber 256. In addition, outlet ports 278 and 280 are located intermediate the buffer gas inlet ports 270 and 274 and the sample gas inlet port 276.

Buffer gas is introduced into the ends of the sample chamber 256 at the first buffer gas inlet port 270 and directed past the second mirror 30 and toward the central portion of chamber 256. Buffer gas is also introduced into the end of sample chamber 256 at the second buffer gas inlet port 274 and directed past the Brewster window 52b of the laser plasma tube 23 toward the central portion of chamber 256. The sample of gas to be analyzed is introduced into the central portion of the chamber 256 through the sample gas inlet port 276. Near the outlet ports 278 and 280, the buffer gas and the sample gas mix. The mixture then exits the sample chamber 256 through the outlet ports 278 and 280. Thus, flow of the buffer gas through the sample chamber 256 forms a "dam" which constrains the gas sample to the portion of the sample chamber 256 located intermediate the outlet ports 278 and 280. Such flow typically creates a region of sub-ambient pressure within the sample chamber. In addition, the flow removes used sample gas to allow new samples to be input for analysis.

Raman scattered light is passed through side windows (not shown) into the channels 266a–h. As in the enclosed gas sample chamber embodiment 154, these side windows may either be continuous along the length of the artificial chamber 256 or they may be discrete windows mounted at the ends of the channels 266. Again, the side windows may advantageously be coated with a high efficiency broadband anti-reflection coating and/or a V-band dielectric coating to reject laser wavelength light.

Referring again to FIGS. 1 and 2, a plurality of detection channels 70a through 70g, referred to herein as 70, are arranged about the gas sample chamber 54. It will be understood that either type of gas sample chamber 154 or 254 could advantageously be utilized when referring to the schematically illustrated gas sample chamber 54. Detectors 72a through 72f, referred to herein as 72, are positioned within the detection channels 70 to optimally detect light scattered from the gases in the sample chamber 54. Typically, the detection channels 70 are aligned perpendicular to the light beam 32.

Any type of detector 72 utilizing photon counting or photocurrent electronics, such as a photodiode, an intensified diode array, a charge coupled device, or a photomultiplier tube, may be employed in the present invention. For simplicity, a photodetector will be discussed herein. It will be understood that this is not a limitation of the present invention.

Detection channels 70 may be advantageously located opposite one another on both sides of the gas sample chamber 54, as are channels 70a and 70e and channels 70b and 70f. Alternatively, a single channel 70b may be located on one side of the light beam 32 with a mirror 70g opposite the channel 70b to re-direct light which was scattered toward the mirror 70g back towards the detection channel 70b. Mirror 70g may be either a planar mirror or a focusing mirror. A single detector channel 70d may also be located to one side of the laser beam 32 without a corresponding channel on the opposite side of the beam 32.

Figure 6:
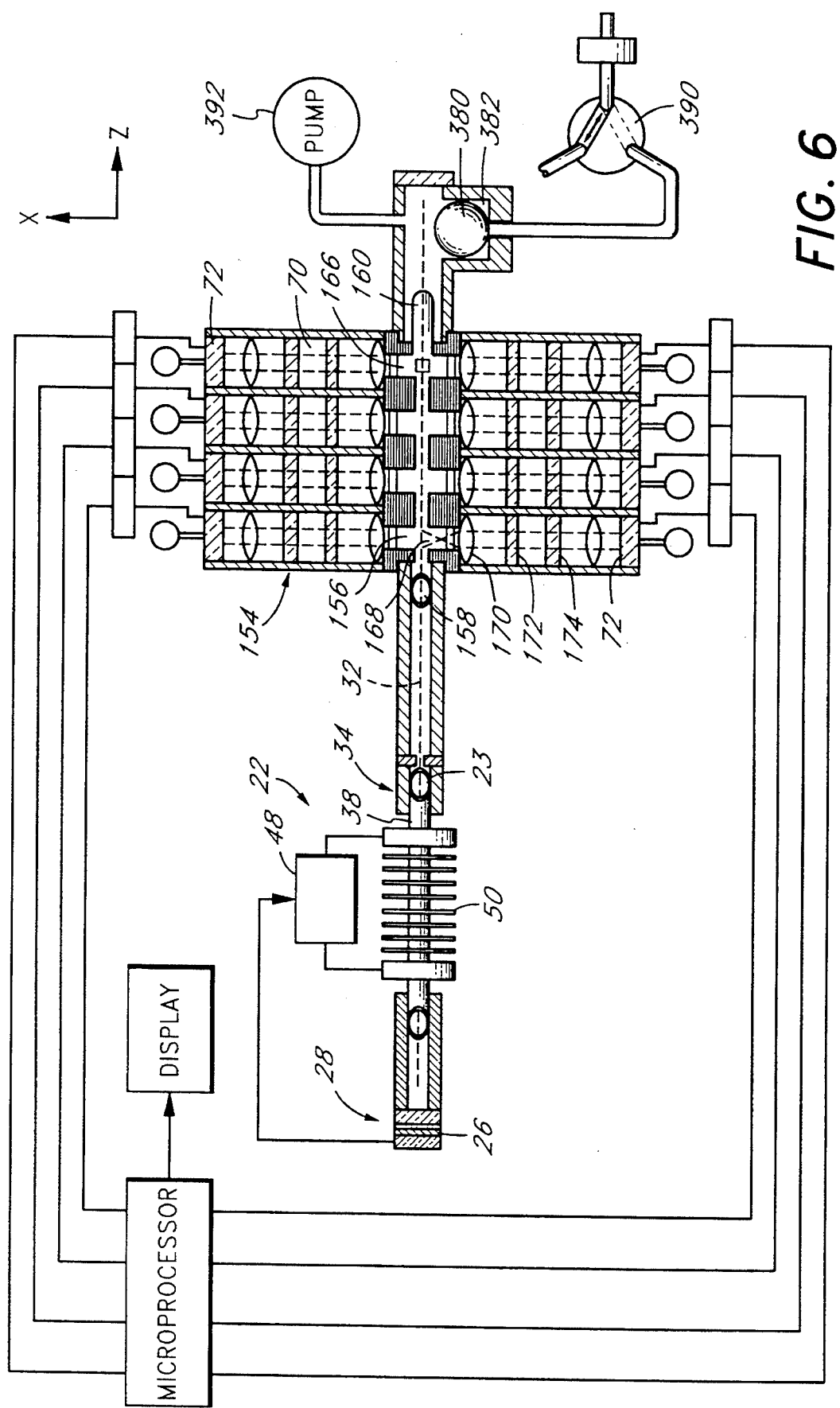
FIG. 6 shows a schematic diagram of a complete laser-activated Raman scattering system which incorporates the present invention.

FIG. 6 shows a schematic diagram of a complete laser-activated Raman scattering system which incorporates zero calibration in accordance with the present invention. Channels 166 of gas sample chamber 154 are generally aligned with detection channels 70. Laser light Raman scattered from gas within chamber 156 traverses through channels 70 and onto detectors 72. Alternatively, optics 170 which collect Raman scattered light onto the detectors 72 in the detection channels 70 could be advantageously utilized instead of windows 168. Typically, filters 172, 174 are placed between each detector 72 and the laser beam to remove energy at the wavelength of the incident laser beam. This improves the signal to noise ratio at the detectors 72.

When the laser beam 32 is activated, intense coherent light, generally at a single wavelength, will be incident on the gas sample. Since rotational/vibrational energy modes are quantized, when a photon strikes a particular gas, the energy exchange will be quantized. The quantization is species specific, i.e., each gas typically has different quantization of energy modes. By observing the frequency shift, or correspondingly the wavelength shift, of scattered photons, it is possible to identify the type of gas which a photon has struck. Gases which are more concentrated have a higher probability of being hit by an incident photon. Thus, by observing the quantity of each group of frequency shifted scattered photons, it is possible to determine the concentration of each gas within the sample.

Identification of a particular gas is accomplished by comparing the measured frequency shift to a known frequency shift. However, such identification could require a large number of comparisons before determining which gas caused a particular frequency shift in photons incident at the laser wavelength. Thus, the constituency of a gas sample is typically assumed to be among a predetermined group. This is usually an accurate assumption since the source of a gas sample is often known to produce only certain gases. Filters for each gas in this predetermined group are placed between the laser beam 32 and as many detectors 72 as there are possible gases in the predetermined group. Each filter removes generally all but one expected Raman scattered wavelength, i.e., Raman line. Thus, each filter and detector 72 combination is dedicated to sensing one type of gas, i.e., dedicated to sensing photons having their frequency shifted a known amount determined by the type of gas with which the photon is expected to collide. By comparing the signals measured at each dedicated detector 72, the concentration of a plurality of gases in a gas sample may be determined simultaneously.

As discussed previously, in addition to intense, coherent light, laser gain mechanisms 22, such as the laser plasma tube of the gas laser discussed herein, often emit light at non-lasing wavelengths which does not get amplified in the laser resonator cavity 24 but still passes through the sample of gas. This non-gain wavelength light is called glow or plasma glow and may create noise in the measured signal. Some of this light might be at wavelengths within the band of one of the intermediate filters arranged to transmit particular Raman lines to particular detectors 72. This will cause the Raman signal at that line to erroneously appear more intense, indicating a greater concentration of a particular gas than is actually present in the sample, i.e., background noise.

Another source of background noise in the measured signal is inherent photodetector 72 dark noise, or dark current. Dark noise is due to random thermal excitation of electrons within detector 72, as well as excitation by cosmic rays and radioactive bombardment. Photodetector 72 dark noise also results in background noise in the measured signal.

Background noise due to both the photodetector 72 dark noise and plasma glow should be removed from a measured signal for accurate absolute Raman scattering intensity measurements. A zero-calibration level is determined as a measure of the background noise. Then, the origin of the intensity measurement scale is set equal to the zero-calibration level, essentially removing from the measurement the background noise due to plasma glow and dark current as well as other consistent sources of noise, such as ambient light.

Determination of the zero-calibration level is performed in the present invention by preventing the laser from lasing without terminating transmission of light into the sample chamber 54 from the laser plasma tube 22. This is accomplished via the introduction of losses into the resonator cavity 24, i.e., degrading the "Q" of the cavity, thus reducing and ultimately preventing lasing action. The resultant signal is then measured at the detectors is then measured as the background level.

By preventing lasing but allowing both the laser plasma tube 22 and each detector 72 to function at the same level as when laser gain is permitted, both plasma glow and dark noise are still measured at each detector 72. The signal level seen by each detector 72 under these circumstances is very similar to the signal level that each detector 72 would see when the laser is lasing and the concentration of the gas to be analyzed in the sample chamber 54 is zero. However, any gas may be located in the sample chamber 54 without diminishing the accuracy of the zero-calibration. Thus, the sample gas need not be absent from the sample chamber for this type of zero-calibration.

Several methods and apparatuses according to the present invention exist for preventing lasing while the laser plasma tube 22 is operating and transmitting light into the sample chamber 54. Referring back to FIGS. 1 and 2, a polypropylene (or other material) ball 380 is introduced into the path of the laser beam 32. This prevents reflection of light from the second mirror 30 of the laser resonator cavity 24, interrupting the feedback which leads to lasing. Since the laser plasma tube 22 is still operating, photons are still emitted towards the gas sample. Thus, although the ball 380 prevents laser feedback, light due to plasma glow will be as intense in the absence of laser light as it is when the laser is lasing. Additionally, light due to dark noise will be measured at each photodetector 70. Elastic scattered light from the laser is rejected by the filters and can be ignored, so the light which is not generated by Raman scattering is thus measured, allowing a zero-calibration level to be determined.

The ball 380 is pneumatically inserted into the path of the laser beam 32 from a recessed cavity 382, as shown in the side view of FIGS. 2 and 5, via air pressure. When an enclosed gas sample chamber 154 is employed in the Raman spectroscopy system, as shown in FIG. 6, a valve 390 located adjacent the ball 380, is opened, allowing a pump 392 to force air to be incident on the ball 380. The force thus created on the ball 380 causes the ball 380 to leave the cavity 382 and enter far enough into the path of the laser beam 32 to prevent lasing. As long as the pump 392 is active at a suitable pressure, the ball 380 remains suspended in the path of the laser beam 32. Air used to suspend the ball 380 does not affect either the gas sample enclosed in the central chamber 156 of the gas sample chamber 154 or the lasing gas enclosed in the plasma discharge tube 38.

Alternatively, when the sample chamber utilizes buffer gas flow, as shown in FIG. 5, a valve 400 located adjacent the ball 380, is opened, allowing air at ambient pressure to be incident on a portion of the ball 380. Because the sample chamber 256 is at a sub-ambient pressure, the air at ambient pressure creates a force on the ball 380 and causes the ball 380 to be sucked into the buffer region 258. As long as the valve 400 is open, the ball 380 will remain suspended in the path of the laser beam 32, thereby preventing lasing.

The ball 380 could alternatively be inserted into the path of the laser beam 32 via mechanical means such as an automatically or manually operated lever (not shown).

Although a ball 380 inserted into the path of the laser beam 32 has been described herein, many other methods for preventing lasing will be obvious to those skilled in the art. For example, any type of suitable object may be inserted into the path of the laser beam 32 via different methods, including but not limited to a pump, automatic levers, or even manual means. Another way to prevent lasing while the plasma tube 22 is operational is to locate a mechanical device such as a shutter, closeable iris or plate having a hole such that the laser beam can pass when the device is in an initial position and cannot pass when the device is in another position which obstructs the light from reaching one of the mirrors 26 or 30 that make up the resonator cavity 24. For example, when the shutter is open, normal laser gain will occur. However, when the shutter is closed, the resonant cavity 24 will be interrupted and light will not be reflected back and forth between the resonant cavity mirrors 26 and 30 for laser gain. With the shutter closed, only negligible Raman scattering will occur and the zero-calibration level for light from sources other than Raman scattering may be determined.

A further way to prevent lasing while the plasma tube 22 is operational is to tilt one of the mirrors 26 or 30 at the end of the resonator cavity 24. Tilting the mirror destroys the feedback thus preventing lasing action. Misalignment could be performed mechanically by mounting one mirror on a piezoelectric crystal which moves when electrically stimulated. However, this method requires that the mirror 26 or 30 be carefully realigned after calibration to again allow lasing.

Other methods to prevent lasing include a piezoelectric shutter, located within the laser resonator cavity 24 similarly to the pneumatic ball 380, which moves into the path of the laser beam upon an electric impetus, and thereby blocks the light beam 32. Alternatively, lasing could be suppressed by activating an electromagnetic coil and thereby creating a magnetic field along the axis of the electromagnetic coil which causes a permanent magnet or magnetic material such as steel or iron, located within the field of the electromagnetic coil to move such that it blocks one of the resonator cavity 24 mirrors 26 or 30. A further method to prevent lasing is to change the pressure within the sample chamber enough to cause refraction which will diminish the amount of light reflected within the laser resonator cavity and thereby abort laser gain. Another method of interrupting laser gain is to inflate a balloon such that it expands into the laser beam 32 path. Yet another implementation to destroy laser gain is to cause a bimetallic element placed near the laser beam 32 to bend into the path of the laser beam 32. These alternative methods of preventing lasing are meant to be illustrative and are not intended to limit the present invention.

Figure 7:
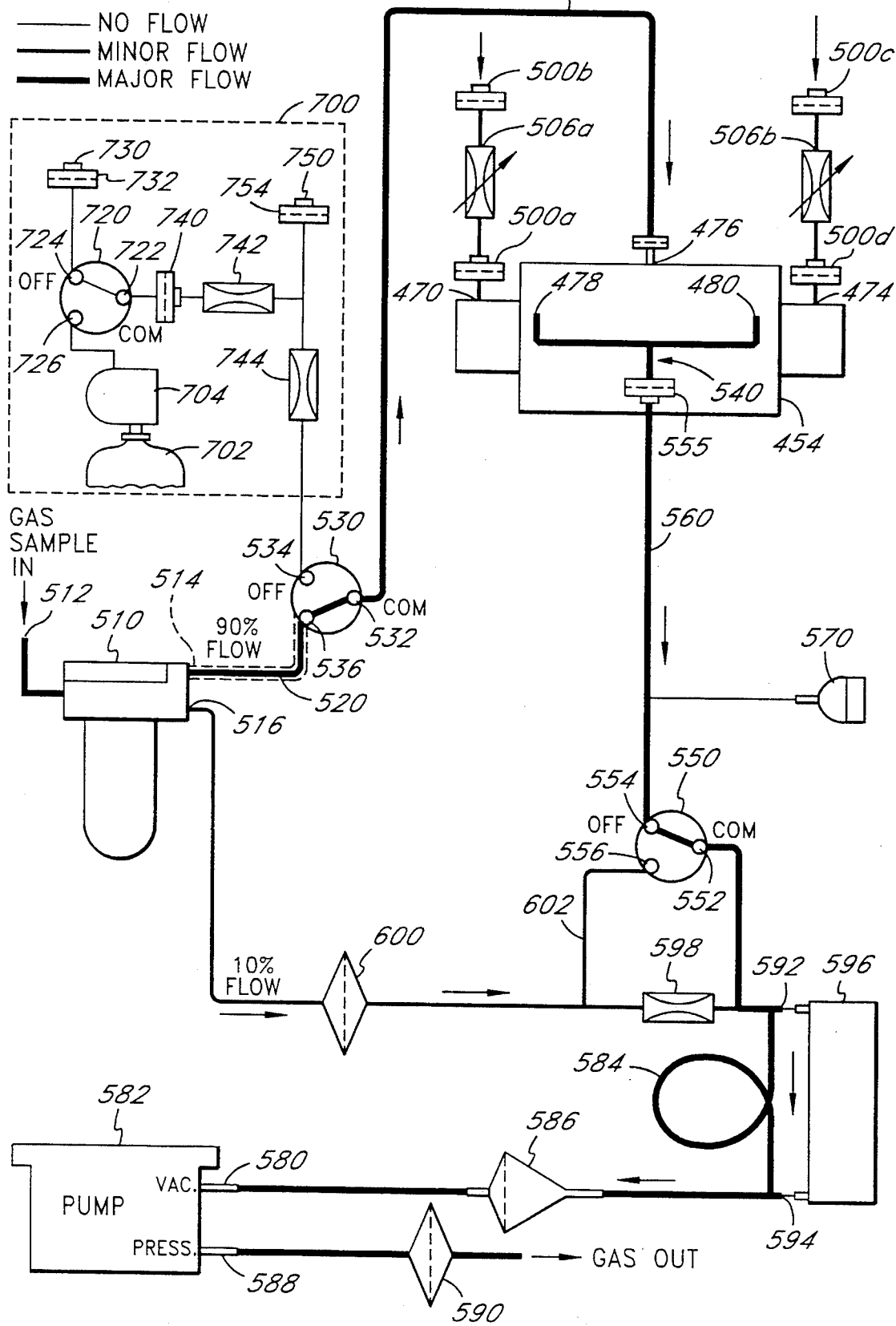
FIG. 7 illustrates, in an argon gas calibration system, the flow of gas through a gas analysis cell and associated control valves while sampling and measuring a sample gas.
Figure 8:
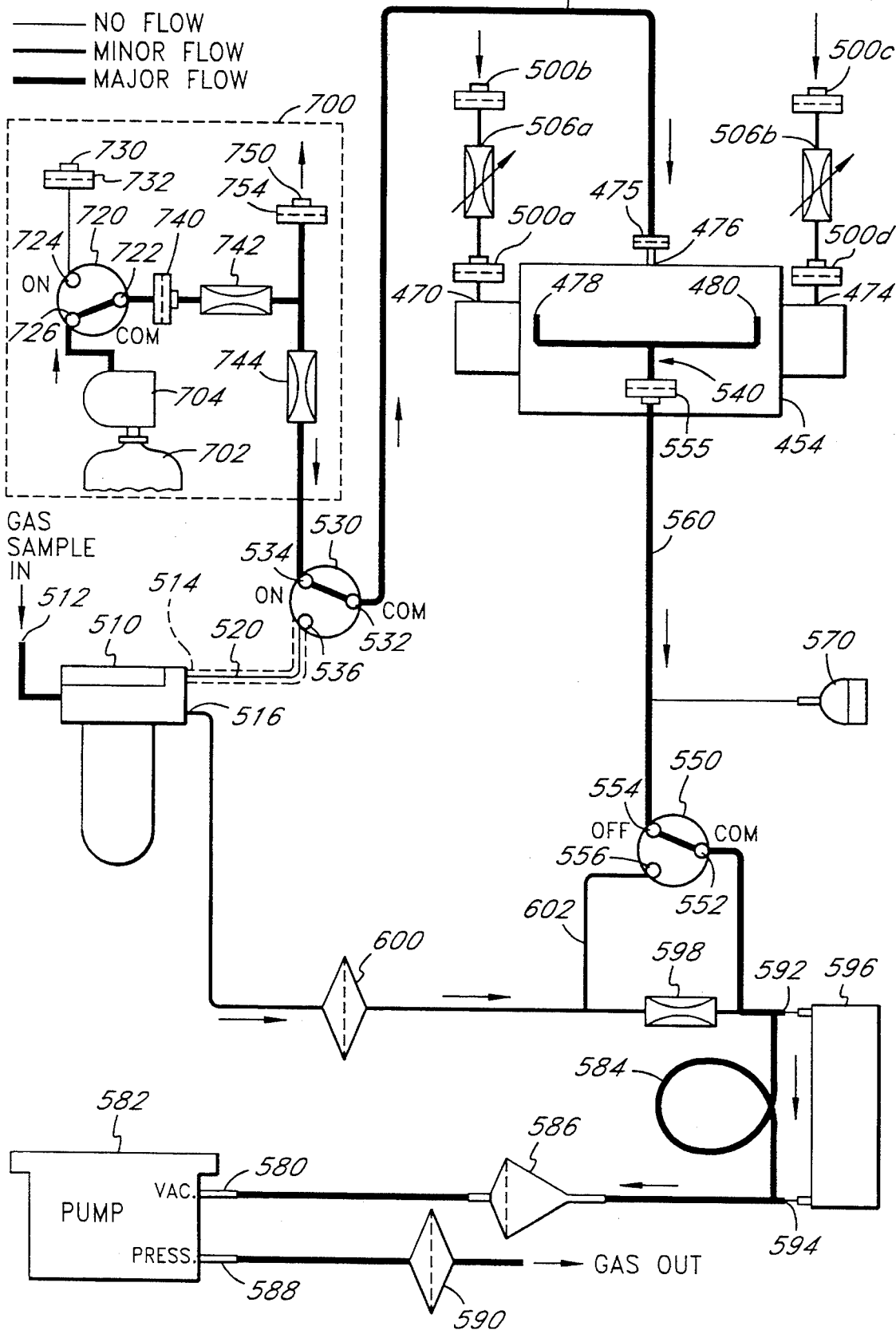
FIG. 8 illustrates, in an argon gas calibration system the flow of gas through a gas analysis cell and associated control valves while performing an argon background calibration.
Figure 9:
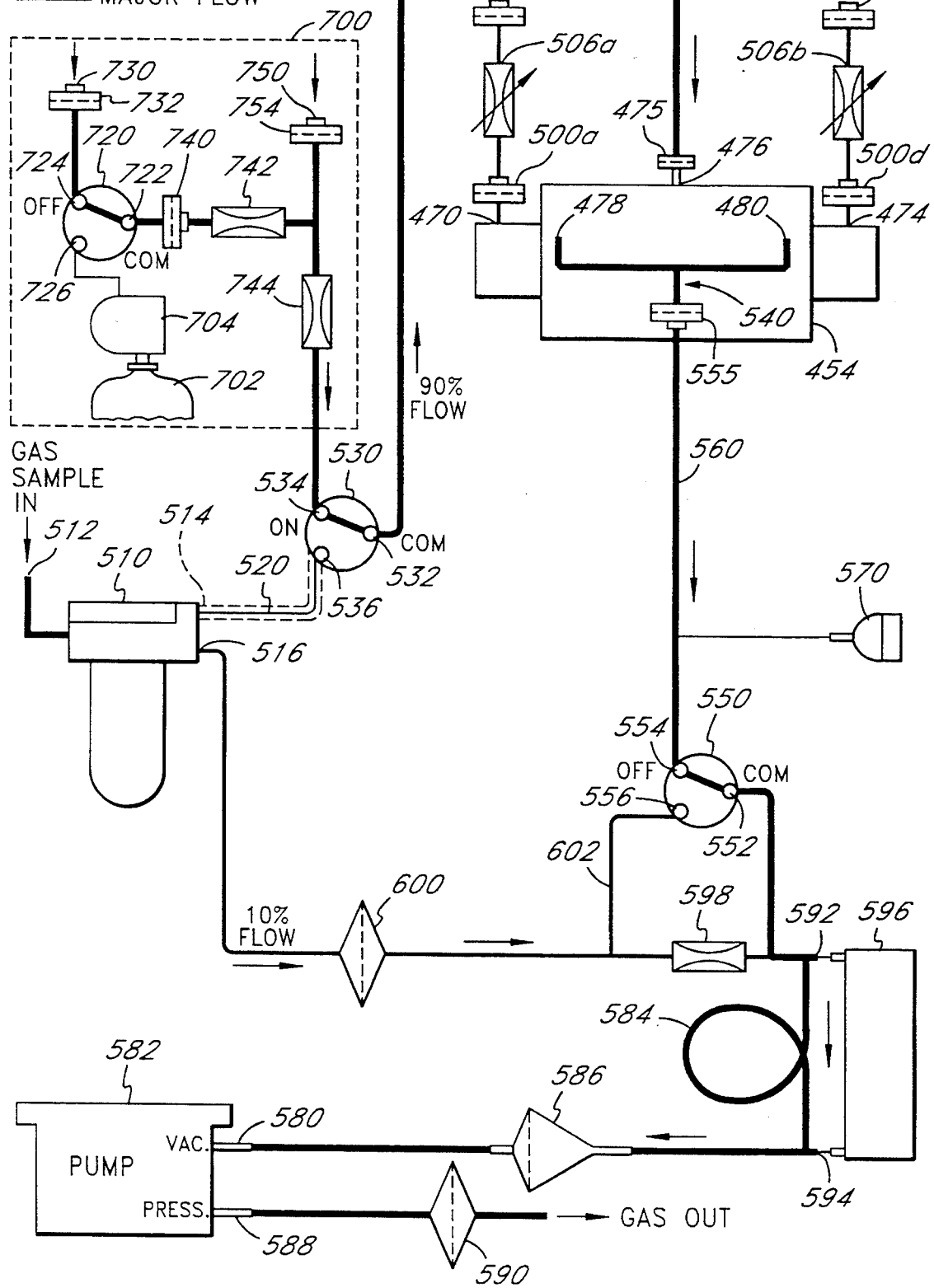
FIG. 9 illustrates, in an argon gas calibration system, the flow of gas through a gas analysis cell and associated control valves while performing a room air calibration.

FIGS. 7-13 illustrate the flow of gas through a gas cell 454 under various conditions. FIGS. 7, 8 and 9 illustrate the gas flows for a system which utilizes argon gas for calibration. FIGS. 10, 11, 12 and 13 illustrate the gas flows for a zero calibration technique which functions by perturbing the resonant conditions within the cavity. In FIGS. 7-13, gas cell 454 is an air dam or buffer gas cell, similar to that shown in more detail in FIG. 5. The laser source and detectors have been omitted from FIGS. 7-13 for clarity. However, it will be understood that these features are present in a complete gas analysis system.

The gas cell 454 in FIGS. 7-13 comprises a sample gas inlet port 476, a first buffer gas inlet port 470, a second buffer gas inlet port 474, and gas outlet ports 478 and 480. Connected to the buffer gas inlet ports 470, 474 are filters 500a, 500b, 500c and 500d and needle valves 506a and 506b, for cleaning and controlling the flow of buffer gas into the gas cell 454 through the first and second buffer gas inlet ports 470 and 474.

A water separator 510 having an inlet port 512 and first and second outlet ports 514 and 516 is connected to the gas cell 454 sample gas inlet port 476 via a section of Nafion ® tubing 520, a calibration valve 530 and a tubing section 531. Calibration valve 530 has a common port 532 which may be selectively connected to a first port 534 or a second port 536.

The Nafion ® tubing section 520 is a perfluorinated ion-exchange membrane prepared from polytetrafluoroethylene and perfluorinated monomers containing sulfonic acid groups. Nafion ® is made by reacting Tetrafluoroethylene (Teflon ®) and Perfluro-3,6 Dioxa-4 Methyl-7 Octensulfonic Acid. Perma Pure Products Inc. of Toms River, N.J., produces tubing from the thermoplastic polymer of the Nafion ® material. After extrusion, the thermoplastic form is converted through a series of chemical reactions into the final acid form which has a high capacity for absorbing and desorbing water. In general, the molecular structure of Nafion ® tubing is:

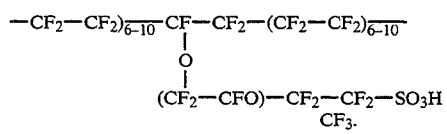

The gas cell 454 gas outlet ports 478 and 480 are connected to a common exhaust port 540 which is connected to a purge valve 550 via a filter 555 and a section of tubing 560. A pressure transducer 570 is connected to tubing 560 for measuring the pressure in the tubing. Purge valve 550 has a common port 552 which may be selectively connected to a first port 554 or a second port 556.

The common port of the purge valve 550 is connected to a vacuum port 580 of a pump 582 via a tubing coil 584 and a hydrophobic filter 586. The pump 582 has a pressure port 588 which exhausts the gas sample through a viral/bacterial filter 590. Flow through the tubing coil 584 is measured by a flow sensor 596 attached to a coil input port 592 and a coil output port 594. The coil input port 592 is also connected to the water separator 510 second outlet port 516 via a purge restrictor 598 and a viral/bacterial filter 600. A bypass line 602 connects the second port 556 of purge valve 550 to the second outlet port 516 via the filter 600.

An argon gas system 700 comprises an argon tank 702 which is connected to an argon valve 720. The argon valve 720 has a common port 722 which may be selectively connected to a first port 724 or a second port 726. An air inlet 730 is connected to the first port 724 via a filter 732. The common port 722 of the argon valve 720 is connected to the first port 534 of the calibration valve 530 via a filter 740, an argon restrictor 742 and a calibration restrictor 744. An air inlet/argon vent 750 is connected intermediate the argon restrictor 742 and the calibration restrictor 744 via a filter 754.

FIG. 7 shows the gas flow through the argon calibration system in normal operation where the gas cell 454 receives the gas sample from the inlet port 512. The gas sample flows through the water separator 510, whereupon the major flow (approximately 90%) of the sample goes through the Nafion ® tubing 520 and the calibration valve 530 into the gas cell 454. The gas sample exits the gas cell 454 via the exhaust port 540, along with some buffer gas, and passes through the purge valve 550, tubing coil 584, hydrophobic filter 586, pump 582 and viral/bacterial filter 590 to exit the system. A minor flow (approximately 10%) of the gas sample flows through the viral/bacterial filter 600 and purge restrictor 598 to join the major flow at the coil input port 592. This minor flow prevents the water separator 510 from becoming clogged with condensed moisture.

FIG. 8 shows the gas flow through the argon gas calibration system during an argon gas background calibration operation where the gas cell 454 receives the argon gas from the argon tank 702 and argon regulator 704. The argon gas is routed through the argon valve 720 from the second port 726 to the common port 722, and then flows through the filter 740, argon restrictor 742 and calibration restrictor 744 into the first port 534 of the calibration valve 530. The argon regulator 704 delivers argon gas under pressure. Excess argon gas flow is vented from the system via vent 750 to prevent air from mixing in with the argon gas sample and to avoid pressurizing the gas cell 454. The argon gas exits the common port 532 of the calibration valve 530 and flows into the gas cell 454 via the sample gas inlet port 476 and a filter 475. The argon gas exits the gas cell 454 via the exhaust port 540, along with some buffer gas, and passes through the purge valve 550, tubing coil 584, hydrophobic filter 586, pump 582 and viral/bacterial filter 590 to exit the system. A minor flow of the gas sample continues to flow through the viral/bacterial filter 600 and purge restrictor 598 to join the argon gas flow at the coil input port 592.

While the gas cell 454 is filled with the argon gas, a calibration is performed to determine a background signal level in the absence of Raman scattering, as there is no Raman scattering from argon.

FIG. 9 shows the gas flow through the argon gas calibration system during a room air calibration operation where the gas cell 454 receives air from the room to calibrate the system for Nitrogen and Oxygen concentration measurements. The major flow of room air enters the system through air inlet 750 and filter 754. A minor flow of room air enters the system through the air input 730 and joins with the major flow after passing through filter 732, the argon valve 720, filter 740 and argon restrictor 742. After joining, the room air flows through the calibration restrictor 744 into the first port 534 of the calibration valve 530. The room air exits the common port 532 of the calibration valve 530 and flows into the gas cell 454 via the sample gas inlet port 476 and a filter 475. The room air exits the gas cell 454 via the exhaust port 540, along with some buffer gas, and passes through the tubing coil 584, hydrophobic filter 586, pump 582 and viral/bacterial filter 590 to exit the system. A minor flow of the gas sample continues to flow through the viral/bacterial filter 600 and purge restrictor 598 to join the room air flow at the coil input port 592.

While the gas cell 454 is filled with the room air, a Nitrogen/Oxygen calibration is performed. Since the concentrations of Nitrogen and Oxygen in air are constant, room air can be used to check and calibrate the system for measurements of these two gases.

Figure 10:
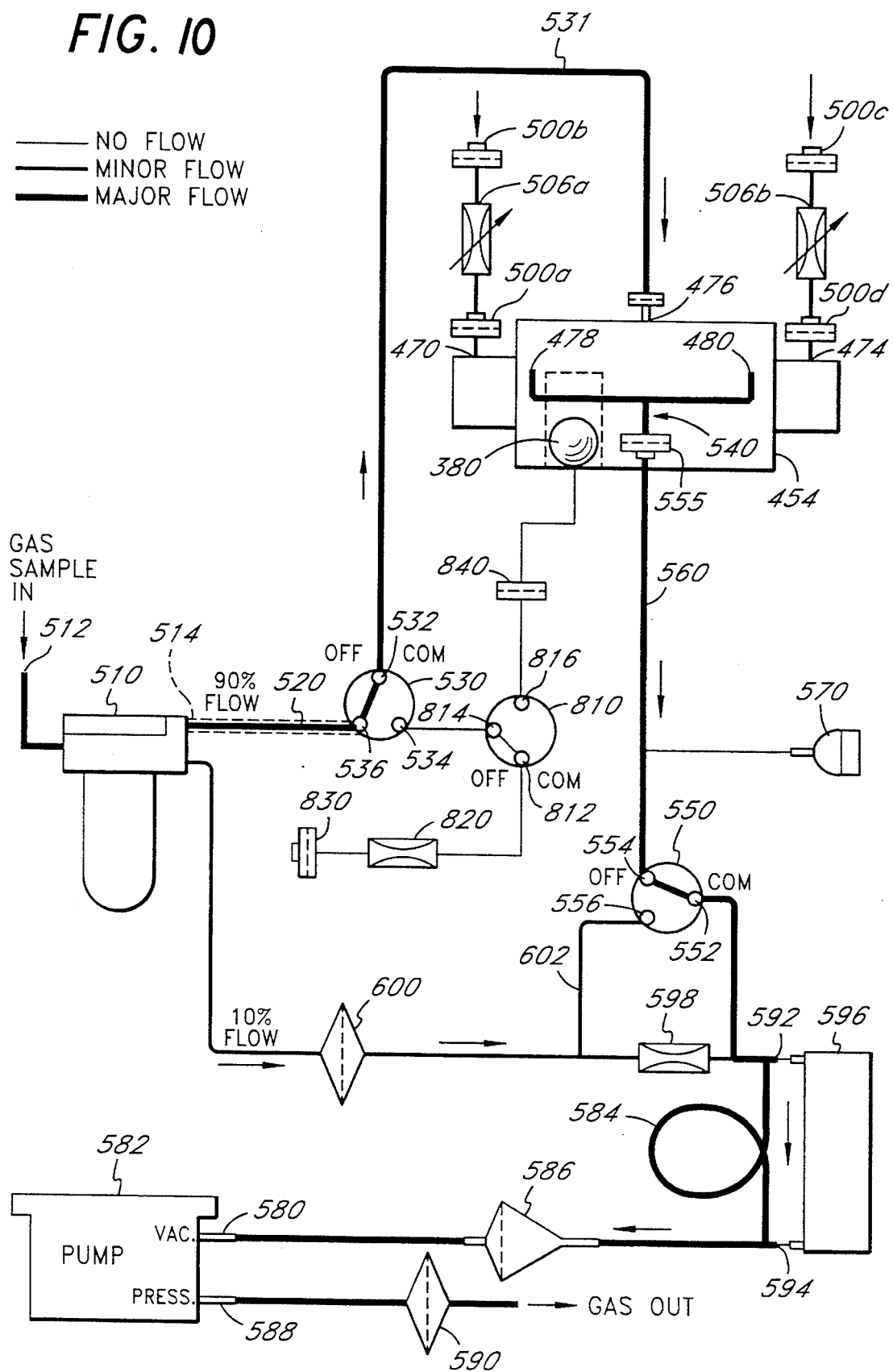
FIG. 10 illustrates, in a beam blocker calibration system, the flow of gas through a gas analysis cell and associated control valves while sampling and measuring a sample gas.

FIG. 10 shows the gas flow through the beam blocker calibration system in normal operation where the gas cell 454 receives the gas sample from the inlet port 512. The gas sample flows through the water separator 510, whereupon the major flow (approximately 90%) of the sample goes through the Nafion ® tubing 520 and the calibration valve 530 into the gas cell 454. The gas sample exits the gas cell 454 via the exhaust port 540, along with some buffer gas, and passes through the tubing coil 584, hydrophobic filter 586, pump 582 and viral/bacterial filter 590 to exit the system. A minor flow (approximately 10%) of the gas sample flows through the viral/bacterial filter 600 and purge restrictor 598 to join the major flow at the coil input port 592. This minor flow prevents the water separator 510 from becoming clogged with condensed moisture.

Figure 11:
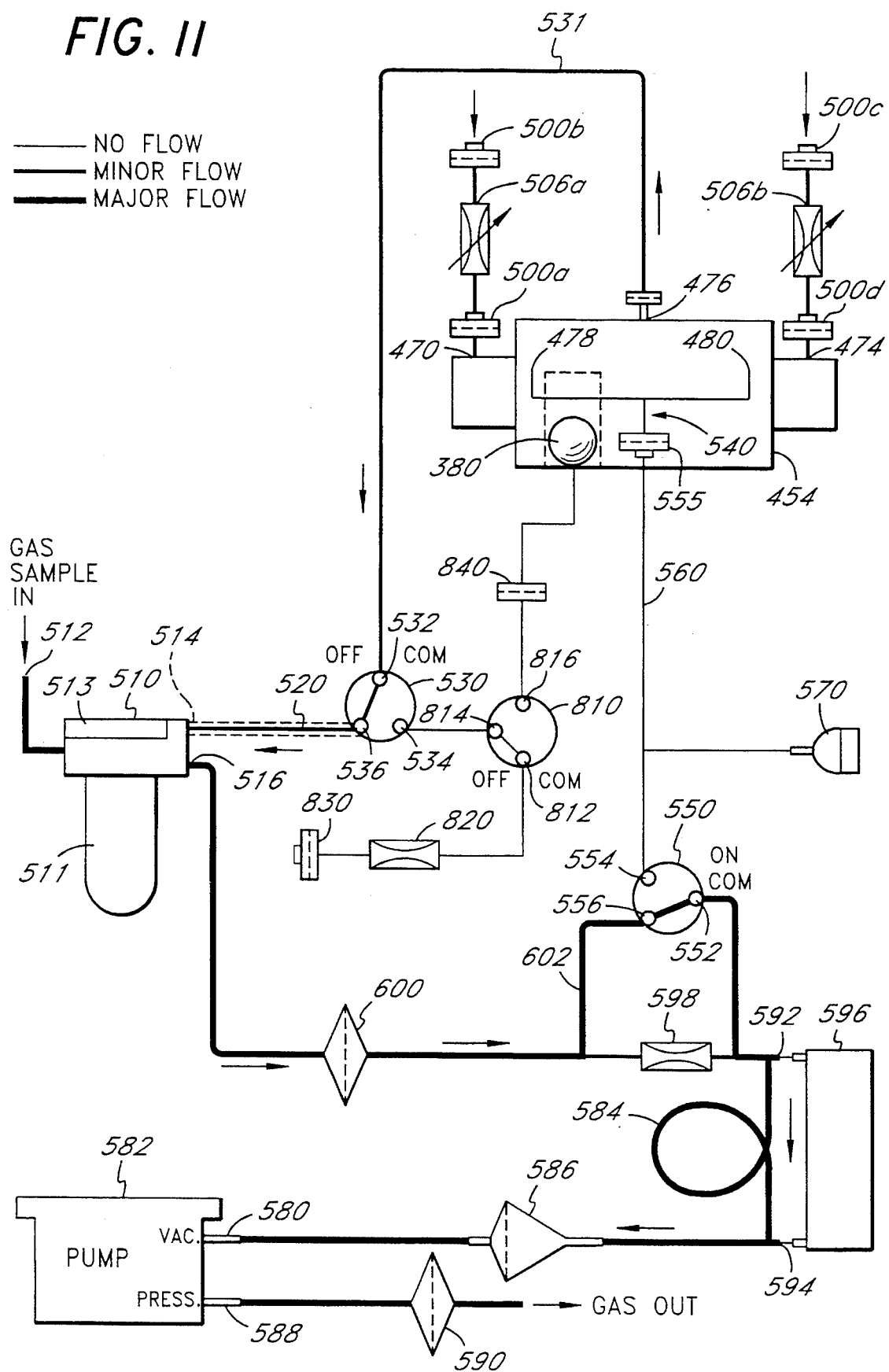
FIG. 11 illustrates, in a beam blocker calibration system, the flow of gas through a gas analysis cell and associated control valves while purging the water trap.

FIG. 11 shows the gas flow through the beam blocker calibration system during a purge cycle of the water trap 510. One type of water trap 510 comprises a collector cup 511 and a hydrophobic membrane filter cartridge 513. As water accumulates in the water separator 510, it may be necessary for the operator to periodically empty the collector cup 511. It may also be necessary to periodically purge the hydrophobic membrane filter cartridge 513 to allow for unrestricted flow. This is accomplished by routing the gas sample flow from the inlet port 512 through the water separator 510 and out of the separator via the second outlet port 516. The purging gas then flows through the viral/bacterial filter 600 and purge valve 550 to the input port 592 of coil 584. A minor flow of the purge gas bypasses the purge valve 550 and flows through the purge restrictor 598 to join the major flow at the coil input port 592. The purge gas then passes through the tubing coil 584, hydrophobic filter 586, pump 582 and viral/bacterial filter 590 to exit the system. During the purge cycle, the gas cell 454 is also purged with buffer gas. Buffer gas enters the gas cell 454 through the buffer gas inlet ports 470, 474 via filters 500a, 500b, 500c and 500d and needle valves 506a and 506b. Gas contained in the gas cell 454, gas outlet ports 478 and 480, common exhaust port 540, purge valve 550, filter 555 and interconnecting tubing including tubing section 560 is drawn out of the gas cell 454 through the gas inlet port 476. It then flows to the outlet port 514 of the water separator 510 via tubing section 531, calibration valve 530, and Nafion ® tubing 520. At the water separator 510, the purged gases from the gas cell 454 flow backwards through the hydrophobic membrane filter cartridge 513, join with the gases coming from sample inlet 512 and exit the system as described above. During the purge cycle, purge valve 550 has common port 552 connected to second port 556, thus closing first port 554.

Figure 12:
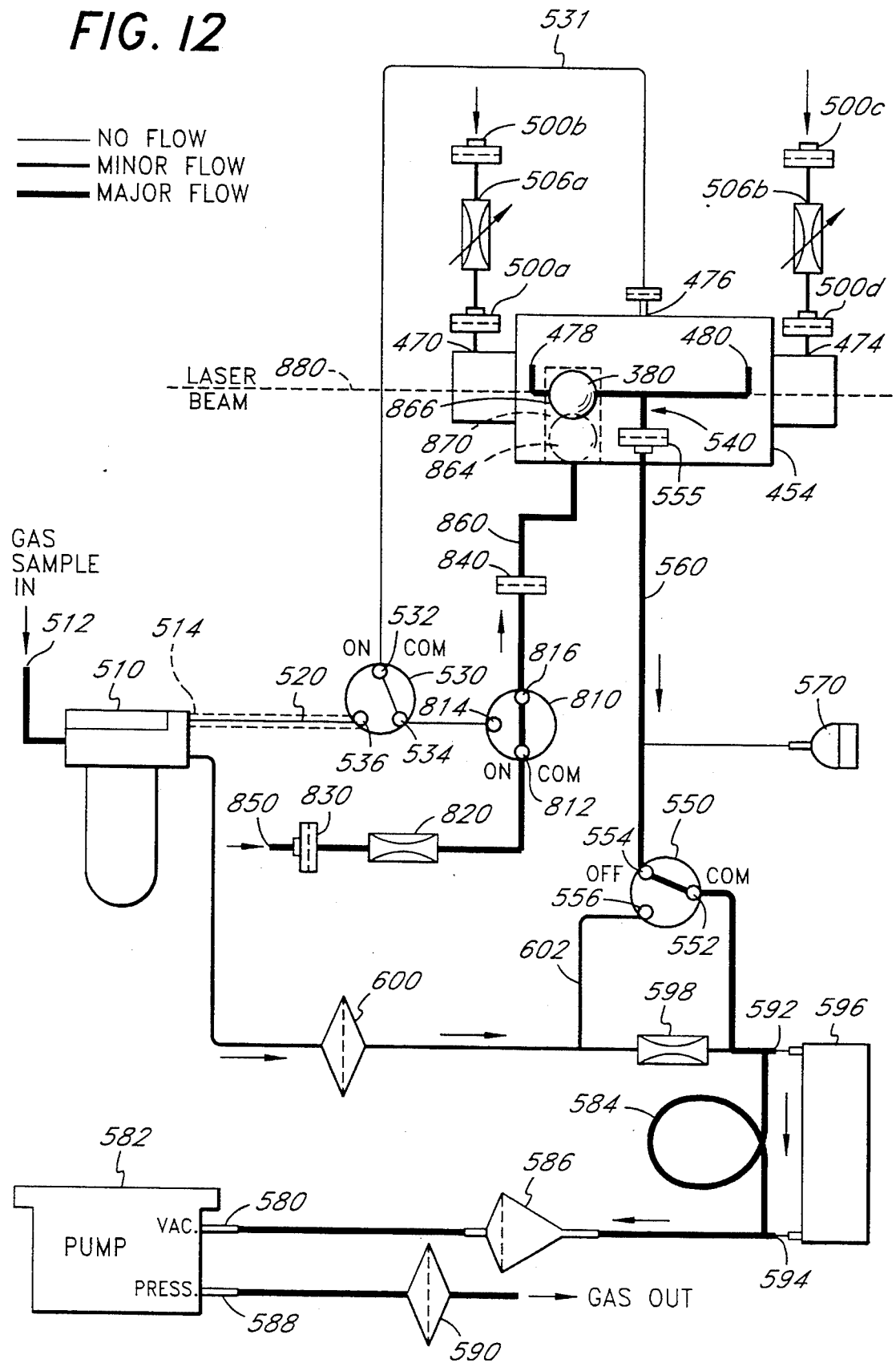
FIG. 12 illustrates, in a beam blocker calibration system, the flow of gas through a gas analysis cell and associated control valves while performing a zero background calibration.

FIG. 12 shows the gas flow through the beam blocker calibration system during the zero background calibration operation. During the zero calibration, the flow of sample gas to the gas cell 454 is stopped by connecting the common port 532 of the calibration valve 530 to the first port 534. The laser resonator cavity is made non-resonant by inserting an object in the laser beam, as discussed previously in connection with FIGS. 5 and 6, wherein a ball 380, is inserted into the path of the laser beam. As shown in FIG. 12, the ball 380 is moved from a position 864 in a storage cavity 870, where it does not interfere with the laser beam 880, to a position 866 which is in the laser beam 880, by applying air pressure to the storage cavity 870. Shown in FIG. 12 are the flow patterns for stopping the sample gas flow and moving the ball 380 into the laser beam 880 from the storage cavity 870. Air is applied to the ball storage cavity 870 through an air inlet port 850. The air flows from the inlet port 850 through a filter 830, a flow restrictor 820, a valve 810, a filter 840 and a line 860. After pushing the ball 380 into the laser beam, i.e., position 866, the air flows through the gas cell 454 and exits the gas cell 454 via the exhaust port 540, along with some buffer gas, and passes through the tubing coil 584, hydrophobic filter 586, pump 582 and viral/bacterial filter 590 to exit the system. A minor flow of the gas sample continues to flow through the viral/bacterial filter 600 and purge restrictor 598 to join the air flow at the coil input port 592.

While the ball 380 is blocking the laser beam, a calibration is performed to determine a background signal level in the absence of Raman scattering, as there is no significant Raman scattering from the air. Upon completion of the calibration, the flow of air to the ball storage cavity 870 is stopped, the ball 380 returns to the position 864 via gravity, and the laser cavity again becomes resonant, thereby producing laser light in the gas sample region of the gas cell 454.

Figure 13:
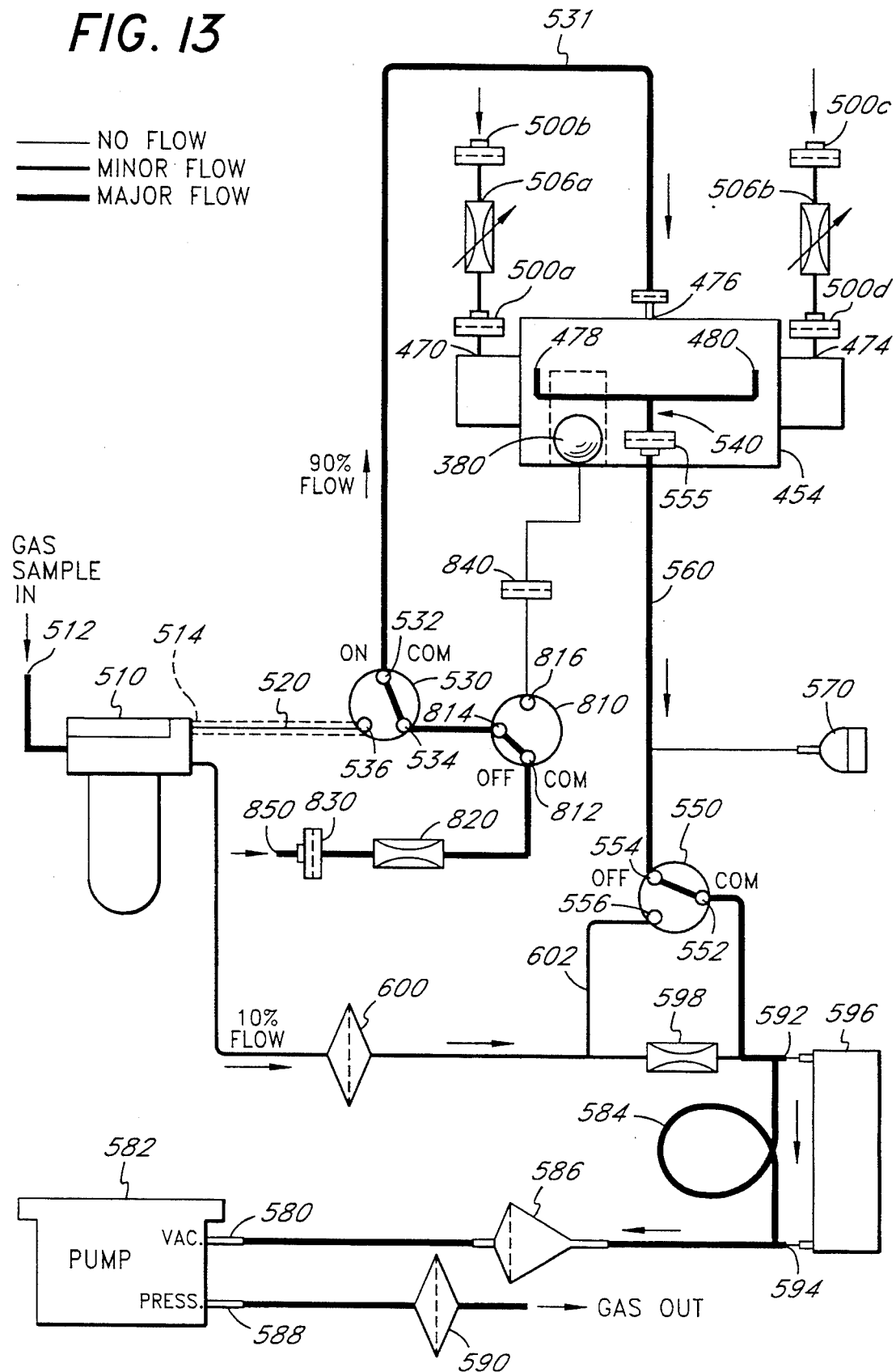
FIG. 13 illustrates, in a beam blocker calibration system, the flow of gas through a gas analysis cell and associated control valves while performing a room air calibration.

FIG. 13 shows the gas flow through the gas cell 454 and associated control valves during a room air calibration operation where the gas cell 454 receives air from the room to calibrate the system for Nitrogen and Oxygen concentration measurements. The major flow of room air enters the system through air inlet 850 and filter 830. The room air flows through the air flow restrictor 820 into the first port 812 of the air calibration valve 810. The room air exits the port 814 of valve 810 and flows through the calibration valve 530 into the gas cell 454 via the sample gas inlet port 476 and filter 475. The room air exits the gas cell 454 via the exhaust port 540, along with some buffer gas, and passes through the tubing coil 584, hydrophobic filter 586, pump 582 and viral/bacterial filter 590 to exit the system. A minor flow of the gas sample continues to flow through the viral/bacterial filter 600 and purge restrictor 598 to join the room air flow at the coil input port 592.

While the gas cell 454 is filled with the room air, a Nitrogen/Oxygen calibration is performed. Since the concentrations of Nitrogen and Oxygen in air are constant, room air can be used to check and calibrate the system for measurements of these two gases.

It will be understood that the method of the present invention for determining a zero-calibration level may be employed with many types of spectroscopy systems, including those utilizing an intracavity laser design. The present invention is particularly well suited for Raman spectroscopy systems. There are numerous embodiments of Raman spectroscopy systems which will be obvious to one skilled in the art, including but not limited to changes in the dimensions of the gas sample chamber, the type of laser, the type of detectors, the location and type of apparatus which prevents optical resonance within the resonant cavity, the number of detection channels, the types of optical elements to direct light, and the types of coatings on such elements. Additionally, one skilled in the art will realize that a single detector with a rotating filter could be used in place of the plurality of detectors. The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. A Raman spectrometer comprising:
a light source for producing light;
a resonant cavity for receiving said light from said light source such that said light resonates within said resonant cavity;
a detector in optical communication with said resonant cavity for receiving Raman scattered light from an analysis sample located within said resonant cavity; and
means for altering the optical characteristics of said resonant cavity such that said light from said light source no longer resonates within said resonant cavity thus reducing the Raman scattered light from said analysis sample detected by said detector to substantially zero.

2. A Raman spectrometer as defined in claim 1 wherein said means for altering the optical characteristics further comprises a blocking device which intercepts said light resonating in said resonant cavity and prevents said light from circulating within said resonant cavity.

3. A Raman spectrometer as defined in claim 1 wherein said resonant cavity further comprises first and second end reflectors.

4. A Raman spectrometer as defined in claim 3 wherein said means for altering the optical characteristics further comprises a blocking device which intercepts said light prior to reaching one of said first and second end reflectors.

5. A Raman spectrometer as defined in claim 1 wherein said light source further comprises a plasma tube.

6. A Raman spectrometer as defined in claim 1 wherein said resonant cavity further comprises a gas sample region for containing a gas sample within said resonant cavity.

7. A spectrometer comprising:
a light source for producing light;
a resonant cavity for receiving said light from said light source such that said light resonates within said resonant cavity;
a detector in optical communication with said resonant cavity for receiving scattered light from an analysis sample located within said resonant cavity; and
means for altering the optical characteristics of said resonant cavity such that said light from said light source no longer resonates within said resonant cavity thus reducing the Raman scattered light from said analysis sample detected by said detector to substantially zero.

8. A spectrometer as defined in claim 7 wherein said means for altering the optical characteristics further comprises a blocking device which disrupts said light resonating in said resonant cavity and prevents said light from circulating within said resonant cavity.

9. A spectrometer as defined in claim 7 wherein said resonant cavity further comprises first and second end reflectors.

10. A spectrometer as defined in claim 9 wherein said means for altering the optical characteristics further comprises a blocking device which intercepts said light prior to reaching one of said first and second end reflectors.

11. A spectrometer as defined in claim 7 wherein said light source further comprises a plasma tube.

12. A spectrometer as defined in claim 7 wherein said resonant cavity further comprises a gas sample region for containing a gas sample within said resonant cavity.

13. A method for calibrating a Raman spectrometer having a resonant cavity comprising the steps of:
   providing a source of light which resonates within said resonant cavity;
   detecting a Raman scattered light intensity from an analysis sample located within said resonant cavity;
   altering the optical characteristics of said resonant cavity so that it is substantially nonresonant, thereby substantially reducing said Raman scattered light intensity from said analysis sample; and
   detecting a background signal level from said substantially nonresonant cavity.

14. A method as defined in claim 13 wherein said step of altering the optical characteristics of said resonant cavity further comprises the step of substantially eliminating the production of predetermined spectroscopy signals, leaving only background and/or noise signals.

15. A method as defined in claim 13 wherein said step of altering said optical characteristics of said resonant cavity reduces said Raman scattered light intensity to substantially zero.

16. A method as defined in claim 13 wherein said step of altering the optical characteristics of said resonant cavity further comprises the step of reflecting optical signals.

17. A method as defined in claim 13 wherein said step of altering the optical characteristics of said resonant cavity further comprises the step of absorbing optical signals.

18. A method as defined in claim 13 wherein said step of altering the optical characteristics of said resonant cavity further comprises the step of diffracting optical signals.

19. A method as defined in claim 13 wherein said step of altering the optical characteristics of said resonant cavity further comprises the step of refracting optical signals.

* * * * *